United States Patent [19]

Walser et al.

[11] 4,111,931
[45] Sep. 5, 1978

[54] 1,2,3,5-TETRAHYDRO-4H-1,5-BENZODIAZE-PINE-4-ONES

[75] Inventors: Armin Walser, West Caldwell; Rodney Ian Fryer, North Caldwell, both of N.J.

[73] Assignee: Hoffmann-La Roche Inc., Nutley, N.J.

[21] Appl. No.: 874,074

[22] Filed: Feb. 1, 1978

Related U.S. Application Data

[62] Division of Ser. No. 775,347, Mar. 7, 1977, Pat. No. 4,080,323.

[51] Int. Cl.$^2$ ............................................. C07D 243/12
[52] U.S. Cl. ........................ 260/239.3 B; 260/239.3 T
[58] Field of Search ................................. 260/239.3 B

[56] References Cited

U.S. PATENT DOCUMENTS

| 4,070,355 | 1/1978 | Vogt | 260/239.3 B |
| 4,075,202 | 2/1978 | Moffett | 260/239.3 B |
| 4,080,323 | 3/1978 | Walser et al. | 260/239.3 B |

*Primary Examiner*—Henry R. Jiles
*Assistant Examiner*—Robert T. Bond
*Attorney, Agent, or Firm*—Samuel L. Welt; George M. Gould; Frank P. Hoffman

[57] ABSTRACT

The present invention concerns compounds of the formula

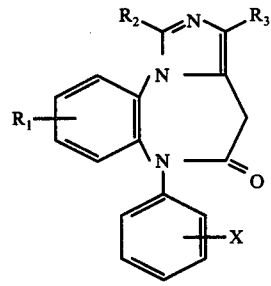

wherein X is hydrogen or halogen; $R_1$ is hydrogen, halogen or trifluoromethyl; $R_2$ is hydrogen or lower alkyl; and $R_3$ is hydrogen, —COO lower alkyl or CON($R_4$)$_2$ wherein $R_2$ is lower alkyl or hydrogen and may be different and the pharmaceutically acceptable salts thereof.

Also provided are methods for the preparation of these compounds as well as pharmaceutical formulations which contain the active compounds of this invention. The compounds of the formula illustrated above are useful as anxiolytics, anticonvulsants, muscle relaxants and sedative agents.

5 Claims, No Drawings

1,2,3,5-TETRAHYDRO-4H-1,5-BENZODIAZEPINE-4-ONES

This is a division, of application Ser. No. 755,347 filed Mar. 7, 1977, now U.S. Pat. No. 4,080,323.

DESCRIPTION OF THE INVENTION

The present invention relates to compounds of the formula

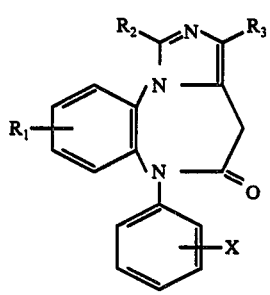

wherein X is hydrogen or halogen; $R_1$ is hydrogen, halogen or trifluoromethyl; $R_2$ is hydrogen or lower alkyl; and $R_3$ is hydrogen, —COO lower alkyl or $CON(R_4)_2$ wherein $R_4$ is lower alkyl or hydrogen and may be different and the pharmaceutically acceptable salts thereof.

By the term "halogen" or "halo" is meant chloro, bromo, iodo and fluoro substituents.

By the term "lower alkyl" is meant both straight chain and branched chain ($C_1$-$C_7$) carbon-hydrogen radicals, preferably $C_1$-$C_4$ carbon-hydrogen radicals, such as methyl, ethyl, propyl, isopropyl and the like.

The compounds of the present invention exhibit pharmacological activity as anticonvulsants, muscle relaxants and sedative agents.

The following reaction schemes set forth the preparative steps required to produce the novel compounds of the present invention.

Scheme 1

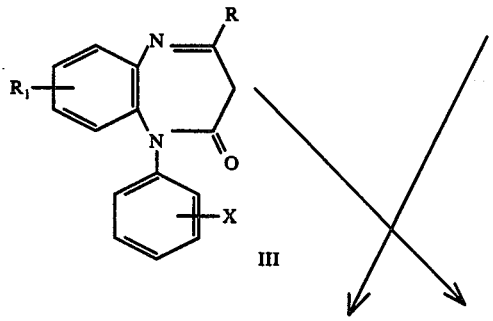

Scheme 1 -continued

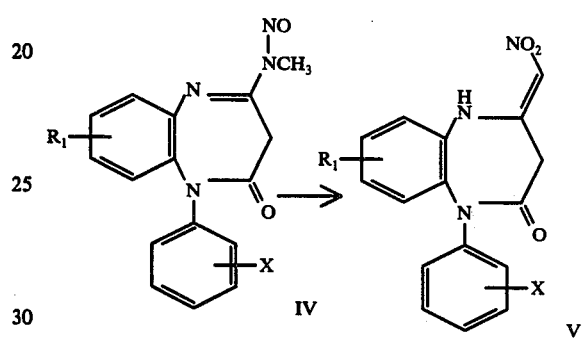

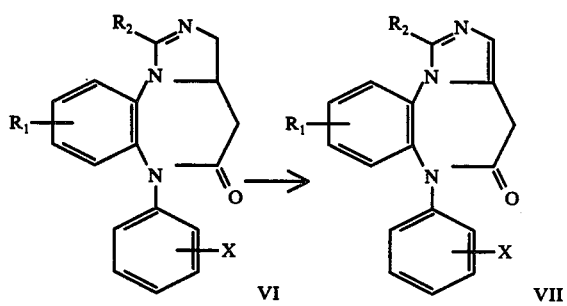

wherein $R_1$, $R_2$ and X are as above and R is the leaving group of the formula $$-O\overset{O}{\underset{\|}{P}}-(NR_5R_6)_2$$

wherein $R_5$ and $R_6$ separately are lower alkyl, phenyl or together with the nitrogen form a substituted or unsubstituted heterocyclic ring of 3–8 atoms, such as pyrrolidine, piperidine and morpholine.

Scheme 2

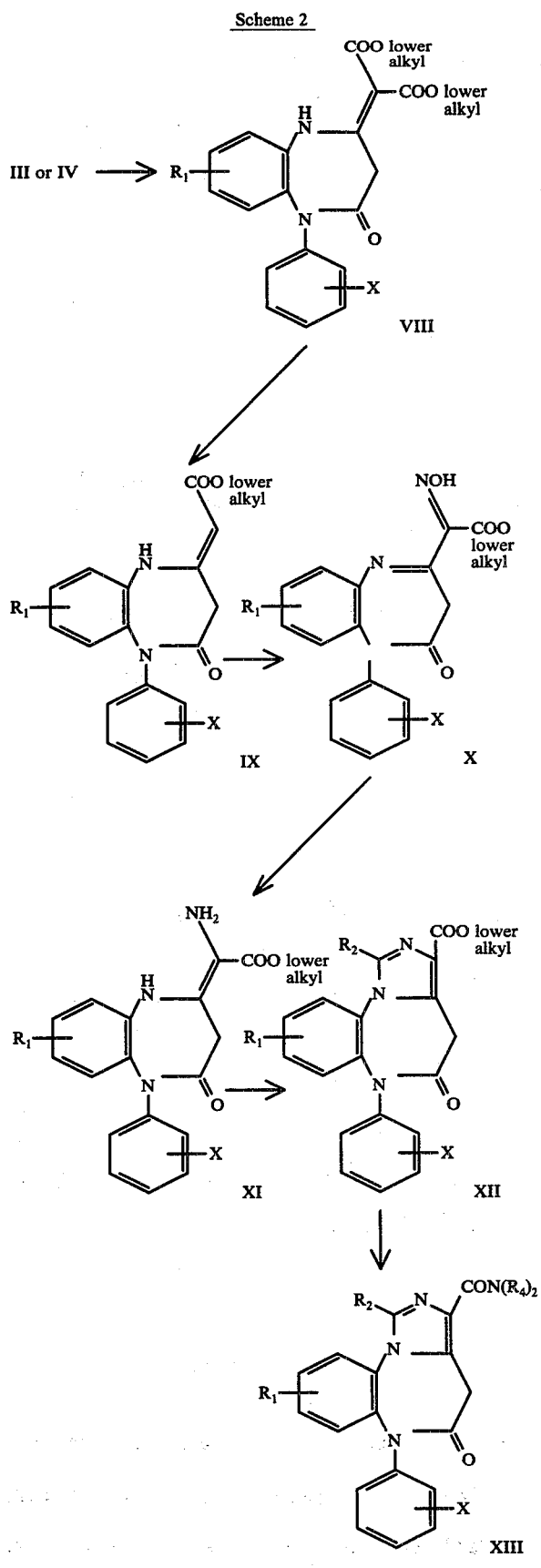

wherein $R_1$, $R_2$, $R_4$ and X are as above.

Scheme 1

I → II

Compounds of formula I which are benzodiazepine-2,4-diones are known compounds, see, for example, South African Patent No. 68/00,803, July 22, 1968 or Chemical Abstracts, 70, 106579, 1969. The diones (I) are converted to the methylamidines by reaction with methylamine and titanium tetrachloride. This reaction is known in the art having been previously set forth in Belgian Pat. No. 774873, Nov. 3, 1971 to Boehringer Ingelheim G.m.b.H.

II → IV

Nitrosation of the compounds of formula II is achieved by the utilization of nitrous acid or nitrosyl chloride in pyridine to form compounds of the formula III. The reaction may be effected in solvents such as aliphatic or aromatic hydrocarbons, e.g., ethers, benzene, toluene, etc., or especially chlorinated hydrocarbons such as methylene chloride. The temperature at which the reaction may be carried out ranges from −30° C. to room temperature with, preferentially, the reaction temperature being about room temperature when utilizing nitrous acid and 0° C. when utilizing nitrosyl chloride.

I → III

The compound of formula I may be reacted with a phosphorylating agent such as a dicyclicaminophosphinic halide, e.g., chloride, or a bis-di-lower alkylaminophosphinic halide, e.g., chloride, after treatment with a strong base sufficient to generate the anion such as alkali metal alkoxides and alkali metal hydrides, e.g., sodium hydride, sodium methoxide or alkyl lithium compounds such as n-butyl lithium. The reaction may be effected at temperatures of 0° C. to 100° C., preferably at room temperature. The reaction is preferably carried out in an aprotic polar inert solvent, such as ethers, e.g., tetrahydrofuran and dioxane and tertiary amides such as dimethylformamide. Examples of the above reaction may be found in Ning et al., Journal of Organic Chemistry, 41, 2724 and 2720 (1976).

III → V

The nucleophilic displacement of the compound of formula III with a carbanion of nitromethane leads to the nitromethylene compound V. The displacement is carried out at temperatures of about −20° to about 100° C., with room temperature as most preferred. As in the above step, an aprotic polar inert solvent may be utilized to solubilize the reaction compounds, e.g., THF, DMF, etc.

IV → V

The compound of the formula IV is thereafter converted to the nitromethylene (V) compound by reaction with nitromethane in the presence of a strong base such as lithium amide, sodium amide, lithium hydride or preferably potassium-t-butoxide. The reaction may be carried out utilizing an inert solvent such as dimethylformamide, dimethylsulfoxide and ethers such as tetrahydrofuran and dimethoxyethane or mixtures thereof. The reaction temperature ranges from −20° to 100° C., but is preferably carried out at room temperature.

V → VI

The compound of the formula V thereafter undergoes a reduction step followed by in situ ring closure by condensation. The reduction step of the reaction is carried out by utilizing hydrogen with a metal catalyst such as platinum, palladium or nickel. Solvents for such a reduction step include hydrocarbons such as alcohols, e.g., ethanol, ethers, e.g., tetrahydrofuran, acetic acid, dimethylformamide, ethyl acetate or mixtures of the above. The reaction temperature ranges from room temperature to 50° C., with room temperature being preferred.

VI → VII

The compound of formula VI is thereafter oxidized with either manganese dioxide or potassium permanganate to the unsaturated compound (VII). Solvents suitable for the oxidation step include any inert aromatic or aliphatic hydrocarbon such as benzene or xylene or chlorinated hydrocarbons such as chlorobenzene. The temperature at which the oxidation takes place may range from 80° C. to 150° C. with the preferred temperature being the reflux temperature of whatever solvent is selected.

III or IV → VIII

The compounds either of formula III or formula IV may be condensed with the anion generated from malonic ester, e.g., of the formula

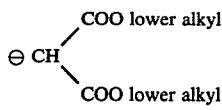

to produce a compound of formula VIII. The anion is generated by deprotonating a malonic ester with a suitable strong base such as alkali metal or alkaline earth metal alkoxides, hydrides or amides. The reaction of the formula IV compound with the malonic ester anion is preferably effected in a solvent such as hydrocarbons, e.g., benzene, toluene, hexane, ethers, e.g., dioxane, THF, diethyl ether, DMF, DMSO, etc., at a range of below room temperature to 150° C., preferably 0° C. to 100° C., most preferably room temperature.

VIII → IX

The compound of formula VIII is thereafter subjected to a hydrolysis and decarboxylation reaction utilizing an alkali metal hydroxide or an alkaline metal hydroxide, such as sodium or potassium hydroxide or calcium or barium hydroxide. The reaction is effected in a solvent such as an alcohol, e.g., methanol or ethanol, or an ether, e.g., dimethoxyethane or tetrahydrofuran. The temperature at which the reaction is run may vary between room temperature to reflux temperature with reflux (varying with the selected solvent) being preferred.

IX → X

The compound of formula IX thereafter undergoes a nitrosation reaction with a reagent such as nitrous acid, nitrosyl chloride or lower alkyl nitrite. The solvents utilized in the reaction may be chlorinated hydrocarbons, e.g., dichloromethane, chlorobenzene, acetic acid or mixtures of water or alcohols, e.g., methanol or ethanol, with the acetic acid being preferred. The reaction temperature may range from −20° C. to 100° C., but room temperature is preferred.

X → XI

The compound of formula X is thereafter reduced to the amino compound (XI) by utilizing either hydrogen with Raney nickel or zinc in acetic acid. Solvents for this reaction include chlorinated hydrocarbons, e.g., dichloromethane, chlorobenzene, alcohols, e.g., methanol or ethanol, acetic acid, dimethylformamide, or ethers, e.g., tetrahydrofuran or dioxane. The reaction temperature may vary from room temperature to 80° C. with room temperature preferred when Raney nickel/$H_2$ is utilized and reflux temperature when zinc/acetic acid are utilized.

XI → XII

The compound of the formula XI thereafter undergoes a ring closure by condensation with an ortho ester of formula XIV, i.e., $R_2-C(OR_1)_3$, or an orthoamide of formula XV, i.e.,

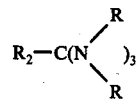

or amide acetal of formula XVI, i.e.,

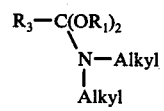

Solvents for this reaction include hydrocarbons, chlorinated hydrocarbons, alcohols, ethers, esters, DMF and acetic acid. The reaction may be carried out in the absence or presence of a catalyst and in an inorganic or organic acid. The reaction temperature ranges from room temperature to reflux temperature of the solvent with the latter being preferred.

XII → XIII

The cyclized product (XII) is thereafter converted from the ester to the amide for example, to the tertiary amide, by reaction with lithium chloride in hexaalkylphosphorous triamide, e.g., hexamethyl- or hexaethylphosphorous triamide. The reaction temperature may be between 180° C. to 250° C. with 220°–230° C. as the preferred temperature. Other synthetic procedures, well known in the art, used for the conversion of esters to amides, may, if desired, also be utilized.

The compounds of the present invention exhibit pharmacological activity as anxiolytics, sedatives, muscle relaxants and anticonvulsants. As contemplated by this invention, the novel compounds of the present invention and their pharmaceutically acceptable salts can be embodied in pharmaceutical dosage formulations containing from about 0.1 to about 200 mg., most preferably 1–100 mg., with the dosage adjusted to species and individual patient requirements. The novel compounds and their pharmaceutically acceptable salts can be administered internally, for example, parenterally or enterally, in conventional pharmaceutical dosage forms. For example, they can be incorporated in conventional liquid or solid vehicles such as water, gelatin, starch, magnesium stearate, talc, vegetable oils and the like to provide tablets, elixirs, capsules, solutions, emulsions and the like according to acceptable pharmaceutical practices.

Preferred compounds of the present invention include the following species.

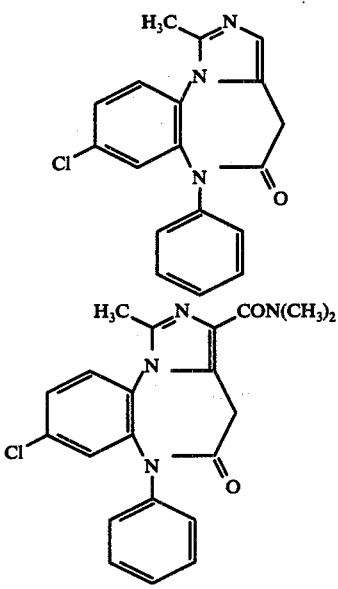

The expression "pharmaceutically acceptable salts" is used to include both inorganic and organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluenesulfonic acid and the like. Such salts can be formed quite readily by those skilled in the art, with the prior art and the nature of the compound to be placed in salt form, in view.

The following examples are illustrative of the present invention and are not intended to limit the scope thereof.

EXAMPLE 1

3,5-Dihydro-2-methylamino-5-phenyl-4H-1,5-benzodiazepin-4-one

A mixture of 28.8 g (0.114 m) of 5-phenyl-2,3,4,5-tetrahydro-1H-1,5-benzodiazepine-2,4-dione[1] in 1 l. of tetrahydrofuran and 200 ml of benzene was stirred in an ice bath and saturated with methyl amine gas until all material was in solution. A mixture of 26 g (0.136 m) of titanium tetrachloride in 200 ml of benzene and was added dropwise. When the addition was complete, the mixture was stirred for ½ hour on ice. The ice bath was then replaced with a heating mantel and the mixture was stirred and refluxed for 2 hours, then cooled and diluted carefully with 200 ml of water.

[1]S. African Patent 68/00, 803, July 22, 1968, Boehringer Ingelheim G.m.b.H, CA 70, 106579 (1969).

The organic layer was decanted off and the residue was washed with tetrahydrofuran and dichloromethane. All the organic layers were combined, dried and evaporated. The residue was crystallized from dichloromethane/hexane to yield the end product with mp 180°–183°.

For analysis, the material was recrystallized from dichloromethane/hexane to give colorless crystals with mp 181°–183°.

Anal. Calcd. for $C_{16}H_{15}N_3O$: C, 72.43; H, 5.70; N, 15.84. Found: C, 72.37; H, 5.73; N, 16.13

EXAMPLE 2

7-Chloro-3,5-dihydro-2-(N-nitrosomethylamino)-5-phenyl-4H-1,5-benzodiazepin-4-one (A) A rapidly stirred solution of 40 g (0.134 m) of 7-chloro-3,5-dihydro-2-methylamino-5-phenyl-4H-1,5-benzodiazepin-4-one[2] in 400 ml of dichloromethane and 40 ml of pyridine was cooled for 15 minutes on an ice bath. Nitrosyl chloride gas was then introduced across the surface of the mixture until all starting material was consumed according to thin layer chromatogram. The mixture was then washed with water and saturated sodium bicarbonate solution, dried and evaporated under reduced pressure. The residue was dissolved in 300 ml of toluene and again evaporated. Crystallization of the residue from ether/hexane yielded end product with mp 123°–126° C.

[2]Belg. Patent No. 774873, Nov. 3, 1971, Boehringer Ingelheim G.m.b.H.

The analytical sample was recrystallized from methylene chloride/hexane to give light yellow crystals with same mp.

Anal. Calcd. for $C_{16}H_{13}ClN_4O_2$: C, 58.46; H, 3.99; N, 17.04 Found: C, 58.51; H, 3.76; N, 17.21.

(B) Sodium nitrite, 21.26 g (0.308 m) was added over a period of 20 min to a stirred solution of 71 g (0.237 m) of 7-chloro-3,5-dihydro-2-methylamino-5-phenyl-4H-1,5-benzodiazepin-4-one in 500 ml of acetic acid. Following the addition, the mixture was stirred for 1 hr at room temperature and was then diluted with 1.5 l. of water. The precipitated product was collected, washed with water and dissolved in methylene chloride. The solution was washed with saturated sodium bicarbonate solution, dried over sodium sulfate and evaporated. The residue was crystallized from ether to yield yellow crystals with mp 121°–124°. A second crop was obtained from the mother liquor.

EXAMPLE 3

3,5-Dihydro-2-(N-nitrosomethylamino)-5-phenyl-4H-1,5-benzodiazepin-4-one

Sodium nitrite, 5.9 g (0.086 moles), was added in 3 portions over a period of 30 minutes to a stirred solution of 18.9 g (0.071 m) of 3,5-dihydro-2-methylamino-5-phenyl-4H-1,5-benzodiazepin-4-one in 200 ml of acetic acid. After the addition was completed, the mixture was stirred for 20 minutes at room temperature and was then diluted with water and extracted with methylene chloride. The methylene chloride extracts were combined, washed with saturated sodium bicarbonate solution, dried and evaporated. The residue was crystallized from ether to yield product. Additional material was obtained from the concentrated mother liquors. For analysis, the material was recrystallized from ethyl acetate/hexane, mp 139°–140° C.

Anal. Calcd. for $C_{16}H_{14}N_4O_2$: C, 65.30; H, 4.79; N, 19.03. Found: C, 65.50; H, 4.65; N, 19.24.

EXAMPLE 4

7-Chloro-5-phenyl-1,2,3,4-tetrahydro-2-nitromethylene-5H-1,5-benzodiazepin-4-one Potassium t-butoxide, 10.24 g (0.092 moles) was added to a mixture of 250 ml of dimethylformamide and 50 ml of nitromethane. After stirring at room temperature for 15 min under nigrogen, 25 g (0.076 m) of 7-chloro-3,5-dihydro-2-(N-nitrosomethylamino)-5-phenyl-4H-1,5-benzodiazepin-4-one was added and stirring was continued for an additional 19 hours. The mixture was acidified with acetic acid and diluted with water. The precipitate was filtered off, washed with water and recrystallized from methylene chloride/ethanol to give pale yellow crystals with mp 259°–261°.

For analysis the product was recrystallized from the same solvents, mp 260°–262°.

Anal. Calcd. for $C_{16}H_{12}ClN_3O_3$: C, 58.46; H, 3.37; N, 12.78. Found: C, 58.58; H, 3.40; N, 12.93.

EXAMPLE 5

5-Phenyl-1,2,3,4-tetrahydro-2-nitromethylene-5H-1,5-benzodiazepin-4-one

Potassium t-butoxide, 3.15 g (0.0281 moles) was added to a mixture of 70 ml of dimethylformamide and 14 ml of nitromethane. After stirring for 30 min at room temperature under nitrogen, 6.9 g (0.0234 moles) of 3,5-dihydro-2-(N-nitrosomethylamino)-5-phenyl-4H-1,5-benzodiazepin-4-one, was added and stirring was continued for 48 hours. The mixture was acidified with acetic acid and diluted with water. The precipitate was collected, washed with water and recrystallized from methylene chloride/ethanol to yield end product with mp 231°–234°. Recrystallization for analysis from the same solvents raised the melting point to 233°–235°.

Anal. Calcd. for $C_{16}H_{13}N_3O_3$: C, 65.08, H, 4.44; N, 14.23. Found: C, 65.06; H, 4.42; N, 14.33.

EXAMPLE 6

8-Chloro-1-methyl-6-phenyl-3,3a,4,6-tetrahydro-5H-imidazo[1,5-a][1,5]benzodiazepin-5-one 7-Chloro-5-phenyl-1,2,3,4-tetrahydro-2-nitromethylene-5H-1,5-benzodiazepin-4-one 18.3 g (0.055 mole) was dissolved in 300 ml of dimethylformamide by gentle heating on a steam bath. The solution was cooled to room temperature and 400 ml of ethanol and 55 g of Raney nickel were added. The mixture was hydrogenated at atmospheric pressure for 21 hours. The catalyst was filtered off and washed well with tetrahydrofuran and methylene chloride. The filtrate was evaporated and the residue was dissolved in 325 ml of xylene, and 40 ml of triethyl orthoacetate was added to the solution which was then refluxed for 1 hour. The mixture was evaporated and the residue was crystallized from ethyl acetate to yield end product with mp 248°–251°. The analytical sample was recrystallized from methylene chloride/ethyl acetate to give colorless crystals with mp 250°–252°.

Anal. Calcd. for $C_{18}H_{16}N_3OCl$: C, 66.36; H, 4.95; N, 12.90 Found: C, 66.11; H, 4.94; N, 12.98.

EXAMPLE 7

8-Chloro-4,6-dihydro-1-methyl-6-phenyl-5H-imidazo[1,5-a][1,5]benzodiazepin-5-one A mixture of 7.2 g (0.022 moles) of 8-chloro-1-methyl-6-phenyl-3,3a,4,6-tetrahydro-5H-imidazo[1,5-a][1,5]benzodiazepin-5-one, 45 g of activated manganese dioxide and 1.5 l. of toluene was stirred and refluxed for 45 minutes. The manganese dioxide was filtered off and washed well with tetrahydrofuran and methylene chloride. The filtrate was evaporated and the residue was crystallized from ethyl acetate to yield end product with mp 276°–278° C.

For analysis, the product was recrystallized from methylene chloride/ethyl acetate to give colorless crystals with mp 276°–278°.

Anal. Calcd. for $C_{18}H_{14}ClN_3O$: C, 66.77; H, 4.36; N, 12.98. Found: C, 66.52; H, 4.12; N, 12.89.

EXAMPLE 8

4,6-Dihydro-1-methyl-6-phenyl-5H-imidazo[1,5-a][1,5]benzodiazepin-5-one

Raney nickel, 11 g, was added to a solution of 3.5 g (0.0118 m) of 5-phenyl-1,2,3,4-tetrahydro-2-nitromethylene-5H-1,5-benzodiazepin-4-one in 50 ml of tetrahydrofuran, and 150 ml of ethanol. The mixture was then hydrogenated at atmospheric pressure for a period of 20 hours. The catalyst was filtered off and washed with tetrahydrofuran and methylene chloride. The filtrate was evaporated and the remaining oil (3.1 g) was dissolved in 250 ml of xylene and 6.2 ml of triethylorthoacetate. After heating to reflux with stirring for 30 min, the reaction mixture was evaporated. The residue was dissolved in 200 ml of toluene and 19 g of activated manganese dioxide was added to the solution. The mixture was stirred and refluxed for 30 min. The manganese dioxide was filtered off and washed well with tetrahydrofuran and methylene chloride. The filtrate was evaporated, and the residue was crystallized from ethyl acetate to yield crystals with mp 217°–220°. For analysis, the material was recrystallized from methylene chloride/ethyl acetate to give colorless crystals with mp 221°–223°.

Anal. Calcd. for $C_{18}H_{15}N_3O$: C, 74.72; H, 5.23; N, 14.52. Found: C, 74.94; H, 5.22; N, 14.69.

EXAMPLE 9

7-Chloro-5-phenyl-1,2,3,5-tetrahydro-2-dimethoxymalonylidene-4H-1,5-benzodiazepin-4-one Potassium t-butoxide, 31.9 g (0.285 m) was added to a solution of 156 ml of dimethyl malonate in 750 ml of dimethylformamide. After stirring under nitrogen for 15 min, 78 g (0.237 m) of 7-chloro-3,5-dihydro-2-(N-nitrosomethylamino)-5-phenyl-4H-1,5-benzodiazepin-4-one was added and stirring was continued for 24 hrs at room temperature followed by additional 3 hrs at 50°–60°. The cool reaction mixture was acidified with glacial acetic acid and the product was crystallized by slow dilution with 1.2 l. of water. The crystals were collected and washed with water, ethanol and ether to yield the colorless product with mp 154°–158°. The analytical sample was recrystallized from methanol, mp 155°–158°.

Anal. Calcd. for $C_{20}H_{17}ClN_2O_5$: C, 59.93; H, 4.28; N, 6.99 Found: C, 60.15; H, 4.28; N, 6.95.

EXAMPLE 10

7-Chloro-5-phenyl-1,2,3,4-tetrahydro-2-[(methoxycarbonyl) methylene]-5H-1,5-benzodiazepin-4-one A mixture of 19.8 g (0.049 m) of 7-chloro-5-phenyl-1,2,3,5-tetrahydro-2-dimethoxymalonylidene-4H-1,5-benzodiazepin-4-one, 5.93 g (0.148 m) of sodium hydroxide, and 1.5 l. of methanol, was stirred and refluxed for 2 hours. About 1 l. of methanol was evaporated off and the remaining mixture was diluted with 1.5 l. of water. The precipitate was filtered, washed with water and then recrystallized from methylene chloride/methanol to yield end product with mp 199°–201° C. The analytical sample was recrystallized from the same solvents; mp unchanged.

Anal. Calcd. for $C_{18}H_{15}ClN_2O_3$: C, 63.07; H, 4.41; N, 8.17. Found: C, 63.19; H, 4.39; N, 8.03.

EXAMPLE 11

7-Chloro-3,5-dihydro-alpha-hydroxyimino-4H-5-phenyl-1,5-benzodiazepin-4-one-2-acetic acid, methyl ester Sodium nitrite, 5.21 g (0.075 m) was added in 3 portions over 15 min to a stirred mixture of 19.9 g (0.058 m) of 7-chloro-5-phenyl-1,2,3,4-tetrahydro-2[(methoxycarbonyl)methylene]-5H-1,5-benzodiazepin-4-one, and 300 ml of acetic acid. The mixture was stirred for an additional 15 min at which time the product was precipitating out, and then diluted with water. The precipitate was filtered, washed with water, sucked dry and recrystallized from tetrahydrofuran to yield product with mp 271°–273°. The analytical sample was recrystallized from tetrahydrofuran to give pale yellow crystals with the same mp.

Anal. Calcd. for $C_{18}H_{14}ClN_3O_4$: C, 58.15; H, 3.80; N, 11.30. Found: C, 58.34; H, 3.97; N, 11.30.

EXAMPLE 12

Methyl 8-chloro-4,6-dihydro-1-methyl-6-phenyl-5H-imidazo[1,5-a][1,5]benzodiazepine-5-one-3-carboxylate A mixture of 135 ml of acetic acid and 5 g (0.0134 m) of 7-chloro-3,5-dihydro-alpha-hydroxyimino-4H-5-phenyl-1,5-benzodiazepin-4-one-2-acetic acid, methyl ester was heated just to reflux, and then cooled to 45° C. Methylene chloride, 675 ml, and 27 g of zinc dust were added to the mixture, which was then refluxed for 20 min. The zinc was filtered off and washed with tetrahydrofuran. The filtrate was evaporated to dryness under vacuum with the water bath temperature kept below 50° C. The residue was dissolved in 320 ml of ethyl acetate and 13.5 ml of triethylorthoacetate and the mixture was refluxed for 1 min. The residue was crystallized from ethyl acetate to yield end product having a mp of 217°–221°. The product was recrystallized from methylene chloride/ethyl acetate for analysis to give colorless crystals with the same mp.

Anal. Calcd. for $C_{20}H_{16}ClN_3O_3$: C, 62.91; H, 4.22; N, 11.00 Found: C, 62.83; H, 4.31; N, 10.91.

EXAMPLE 13

8-Chloro-4,6-dihydro-6-phenyl-5-oxo-1,N,N-trimethyl-5H-imidazo[1,5-a][1,5]benzodiazepin-3-carboxamide A mixture of 1.2 g of methyl 8-chloro-4,6-dihydro-1-methyl-6-phenyl-5-oxo-5H-imidazo[1,5-a][1,5]benzodiazepin-3-carboxylate, 2 g of lithium chloride and 12 ml of hexamethyl phosphoric triamide was stirred and heated up to 230°. As soon as this temperature was reached, the reaction mixture was cooled and partitioned between methylene chloride and water. The organic phase was washed with water, dried over sodium sulfate and evaporated. Crystallization of the residue from ether yielded the end product which was recrystallized from ethyl acetate/hexane for analysis, mp 213°–215°.

Anal. Calcd. for $C_{21}H_{19}ClN_4O_2$: C, 63.88; H, 4.85; N, 14.19. Found: C, 63,81; H, 4.81; N, 14.20.

EXAMPLE 14

8-Chloro-4,6-dihydro-6-phenyl-5-oxo-N,N-dimethyl-5H-imidazo[1,5-a][1,5]benzodiazepine-3-carboxamide As described in previous example, 8-chloro-4,6-dihydro-6-phenyl-5-oxo-5H-imidazo[1,5-a][1,5]benzodiazepine-3-carboxylic acid, methyl ester was converted to the dimethylamide, mp. 255°–257°.

EXAMPLE 15

| Capsule Formulation | | | | |
|---|---|---|---|---|
| | mg/capsule | | | |
| 1. 8-chloro-4,6-dihydro-1-methyl-6-phenyl-5H-imidazo-[1,5-a][1,5]benzodiazepin-5-one | 1.0 | 5.0 | 10.0 | 40.0 |
| 2. Lactose | 149.0 | 182.5 | 215.0 | 260.0 |
| 3. Cornstarch | 40.0 | 50.0 | 60.0 | 80.0 |
| 4. Magnesium Stearate | 2.0 | 2.5 | 3.0 | 4.0 |
| 5. Talc | 8.0 | 10.0 | 12.0 | 16.0 |
| Total | 200 mg. | 250 mg. | 300 mg. | 400 mg. |

Procedure:
1. Mix items 1–3 in a suitable mixer. Mill through suitable mill.
2. Mix with items 4 and 5 and fill on capsule machine.

EXAMPLE 16

| Wet Granulation Tablet Formulation | | | | |
|---|---|---|---|---|
| | mg/tablet | | | |
| 1. 8-chloro-4,6-dihydro-1-methyl-6-phenyl-5H-imidazo-[1,5-a][1,5]benzodiazepin-5-one | 1.0 | 5.0 | 10.0 | 40.0 |
| 2. Lactose | 195.0 | 230.0 | 264.0 | 273.0 |
| 3. Pregelatinized Starch | 12.5 | 15.0 | 17.5 | 20.0 |
| 4. Cornstarch | 25.0 | 30.0 | 35.0 | 40.0 |
| 5. Modified Starch | 12.5 | 15.0 | 17.5 | 20.0 |
| 6. Magnesium Stearate | 4.0 | 5.0 | 6.0 | 7.0 |
| Total | 250 mg. | 300 mg. | 350 mg. | 400 mg. |

Procedure:
1. Mix items 1–5 in a suitable mixer, granulate with water. Dry overnight in an oven. Mill through a Fitzpatrick mill.
2. Mix with item 6 and compress on a suitable press.

EXAMPLE 17

| Direct Compression Tablet Formulation | | | | |
|---|---|---|---|---|
| | mg/tablet | | | |
| 1. 8-chloro-4,6-dihydro-1-methyl-6-phenyl-5H-imidazo-[1,5-a][1,5]benzodiazepin-5-one | 1.0 | 5.0 | 10.0 | 40.0 |
| 2. Lactose, Anhydrous DTG | 127.0 | 142.5 | 182.0 | 216.0 |
| 3. Microcrystalline Cellulose | 40.0 | 50.0 | 60.0 | 80.0 |
| 4. Modified Starch | 10.0 | 12.5 | 15.0 | 20.0 |
| 5. Cornstarch | 20.0 | 25.0 | 30.0 | 40.0 |
| 6. Magnesium Stearate | 2.0 | 2.5 | 3.0 | 4.0 |
| Total | 200 mg. | 250 mg. | 300 mg. | 400 mg. |

Procedure:
1. Mix items 1–5 in a suitable mixer for 1 to 15 minutes.
2. Add item 6 and mix for 5 minutes. Compress on a suitable press.

EXAMPLE 18

| Wet Granulation Tablet Formulation | | | | |
|---|---|---|---|---|
| | mg/tablet | | | |
| 1. 8-chloro-4,6-dihydro-1,N,N-trimethyl-6-phenyl-5H-[1,5-a]-[1,5]benzodiazepin-5-one-3-carboxamide | 1.0 | 5.0 | 10.0 | 40.0 |
| 2. Lactose | 195.0 | 230.0 | 264.0 | 273.0 |
| 3. Pregelatinized Starch | 12.5 | 15.0 | 17.5 | 20.0 |
| 4. Cornstarch | 25.0 | 30.0 | 35.0 | 40.0 |
| 5. Modified Starch | 12.5 | 15.0 | 17.5 | 20.0 |
| 6. Magnesium Stearate | 4.0 | 5.0 | 6.0 | 7.0 |

-continued

Wet Granulation Tablet Formulation

| | mg/tablet | | | |
|---|---|---|---|---|
| Total | 250 mg. | 300 mg. | 350 mg. | 400 mg. |

Procedure:
1. Mix items 1–5 in a suitable mixer, granulate with water. Dry overnight in an oven. Mill through a Fitzpatrick mill.
2. Mix with item 6 and compress on a suitable press.

EXAMPLE 19

Direct Compression Tablet Formulation

| | mg/tablet | | | |
|---|---|---|---|---|
| 1. 8-chloro-4,6-dihydro-1,N,N-trimethyl-6-phenyl-5H-[1,5-a]-[1,5]benzodiazepin-5-one-3-carboxamide | 1.0 | 5.0 | 10.0 | 40.0 |
| 2. Lactose, Anhydrous DTG | 127.0 | 142.5 | 182.0 | 216.0 |
| 3. Microcrystalline Cellulose | 40.0 | 50.0 | 60.0 | 80.0 |
| 4. Modified Starch | 10.0 | 12.5 | 15.0 | 20.0 |
| 5. Cornstarch | 20.0 | 25.0 | 30.0 | 40.0 |
| 6. Magnesium Stearate | 2.0 | 2.5 | 3.0 | 4.0 |
| Total | 200 mg. | 250 mg. | 300 mg. | 400 mg. |

Procedure:
1. Mix items 1–5 in a suitable mixer to 1 to 15 minutes.
2. Add item 6 and mix for 5 minutes. Compress on a suitable press.

EXAMPLE 20

Capsule Formulation

| | mg/capsule | | | |
|---|---|---|---|---|
| 1. 8-chloro-4,6-dihydro-1,N,N,-trimethyl-6-phenyl-5H-[1,5-a]-[1,5]benzodiazepin-5-one-3-carboxamide | 1.0 | 5.0 | 10.0 | 40.0 |
| 2. Lactose | 149.0 | 182.5 | 215.0 | 260.0 |
| 3. Cornstarch | 40.0 | 50.0 | 60.0 | 80.0 |
| 4. Magnesium Stearate | 2.0 | 2.5 | 3.0 | 4.0 |
| 5. Talc | 8.0 | 10.0 | 12.0 | 16.0 |
| Total | 200 mg. | 250 mg. | 300 mg. | 400 mg. |

Procedure:
1. Mix items 1–3 in a suitable mixer. Mill through suitable mill.
2. Mix with items 4 and 5 and fill on capsule machine.

We claim:
1. A compound of the formula wherein X is hydrogen or halogen and $R_1$ is hydrogen, halogen or trifluoromethyl.

2. A compound of the formula wherein $R_1$ is hydrogen, halogen or trifluoromethyl and X is hydrogen or halogen.

3. A compound of the formula wherein $R_1$ is hydrogen, halogen or trifluoromethyl and X is hydrogen or halogen.

4. A compound of the formula wherein $R_1$ is hydrogen, halogen or trifluoromethyl and X is hydrogen or halogen.

5. A compound of the formula wherein $R_1$ is hydrogen, halogen or trifluoromethyl and X is hydrogen or halogen.

* * * * *